United States Patent
Vu

(10) Patent No.: US 9,629,972 B1
(45) Date of Patent: Apr. 25, 2017

(54) BILATERAL BITE BLOCK

(71) Applicant: An Binh Vu, Fallbrook, CA (US)

(72) Inventor: An Binh Vu, Fallbrook, CA (US)

(73) Assignee: Dupaco, Inc., Oceanside, CA (US)

( * ) Notice: Subject to any disclaimer, the term of this patent is extended or adjusted under 35 U.S.C. 154(b) by 0 days.

(21) Appl. No.: 14/567,197

(22) Filed: Dec. 11, 2014

Related U.S. Application Data

(60) Provisional application No. 61/915,759, filed on Dec. 13, 2013.

(51) Int. Cl.
*A61M 16/04* (2006.01)

(52) U.S. Cl.
CPC ...... *A61M 16/0493* (2014.02); *A61M 16/049* (2014.02); *A61M 16/0488* (2013.01); *A61M 16/0495* (2014.02); *A61M 16/0497* (2013.01)

(58) Field of Classification Search
CPC .. A61M 16/00; A61M 16/04; A61M 16/0463; A61M 16/0488; A61M 16/049; A61M 16/0493; A61M 16/0495; A61M 16/0497; A61M 25/02; A61M 2025/022; A61F 5/56; A61F 5/566; A61F 2005/563; A63B 71/085; A63B 2071/086; A63B 2071/088; A61C 7/08; A61B 1/24
USPC ................... 128/200.26, 859, 860
See application file for complete search history.

(56) References Cited

U.S. PATENT DOCUMENTS

| | | | | |
|---|---|---|---|---|
| 4,425,911 A | * | 1/1984 | Luomanen | A61M 16/0488 128/200.26 |
| 5,743,254 A | * | 4/1998 | Parker | A61M 16/0488 128/200.26 |
| 2009/0050161 A1 | * | 2/2009 | Burdumy | A61B 13/00 128/861 |
| 2015/0157821 A1 | * | 6/2015 | Manecke | A61M 16/0434 600/114 |

* cited by examiner

*Primary Examiner* — Justine Yu
*Assistant Examiner* — Colin W Stuart
(74) *Attorney, Agent, or Firm* — Edward W. Callan

(57) ABSTRACT

In a bilateral bite block, a broad upper component extends bilaterally between a front end and a back end for overlying a person's tongue and at least some of the person's lower molars and for underlying at least some of the person's upper molars. Molar blocks extend downward from both sides of the broad upper component and are disposed for contacting the person's lower molars. A groove is disposed within a top surface of a handle and the broad upper component for receiving an endotracheal tube. An aperture is disposed within the groove in the broad upper component for grasping a received endotracheal tube that can extend within the groove from the handle to beyond the back end of the upper component so that a received endotracheal tube that extends within the groove can contact the person's tongue and thereby enhance the grasp of the endotracheal tube.

2 Claims, 2 Drawing Sheets

BILATERAL BITE BLOCK

BACKGROUND OF THE INVENTION

The present invention generally pertains to medical apparatus and is particularly directed to apparatus that prevents contact between a person's upper and lower teeth during medical treatment or diagnostic procedure.

One such apparatus is a bite block that is shaped for being positioned between a person's upper molars and lower molars.

SUMMARY OF THE INVENTION

The invention is a bilateral bite block, comprising: a broad upper component extending bilaterally between a front end and a back end of the broad upper component for overlying a person's tongue and at least some of the person's lower molars and for underlying at least some of the person's upper molars when the bilateral bite block is inserted into the person's mouth; molar blocks extending downward from both sides of the broad upper component and disposed for contacting the person's lower molars when the bilateral bite block is inserted into the person's mouth and the person's jaw is closed; and a handle extending from the front end of the broad upper component for use in inserting the bilateral bite block into the person's mouth; wherein there is a groove extending within a top surface of the broad upper component for receiving an endotracheal tube in a position that is laterally disposed approximately midway between the person's molars when the bite block is inserted into the person's mouth and the person's jaw is closed; wherein an aperture is disposed within the groove in the broad upper component for grasping a said received endotracheal tube that has been received within the groove, to thereby inhibit lateral movement of the bilateral bite block; wherein the broad upper surface of the upper component next to the aperture is longitudinally convex to thereby define an aperture for enhancing said grasp of said endotracheal tube; and wherein the aperture passes through the upper component so that said endotracheal tube that extends within the groove can contact the person's tongue and thereby enhance said grasp of said endotracheal tube.

In another aspect, the invention is a bilateral bite block, comprising: a broad upper component extending bilaterally between a front end and a back end of the broad upper component for overlying a person's tongue and at least some of the person's lower molars and for underlying at least some of the person's upper molars when the bilateral bite block is inserted into the person's mouth; molar blocks extending downward from both sides of the broad upper component and disposed for contacting the person's lower molars when the bilateral bite block is inserted into the person's mouth and the person's jaw is closed; and a handle extending from the front end of the broad upper component for use in inserting the bilateral bite block into the person's mouth; wherein there is a groove extending within a top surface of the broad upper component for receiving an endotracheal tube in a position that is laterally disposed approximately midway between the person's molars when the bilateral bite block is inserted into the person's mouth and the person's jaw is closed; wherein an aperture is disposed within the groove in the broad upper component for grasping a received endotracheal tube that has been received within the groove, to thereby inhibit lateral movement of the bilateral bite block; and wherein the aperture passes through the broad upper component so that said endotracheal tube that extends within the groove can contact the person's tongue and thereby enhance said grasp of said endotracheal tube.

Additional features of the invention are described with reference to the detailed description of the preferred embodiments.

In another aspect, the invention is the ornamental design for a bilateral bite block, as shown in the drawing.

DETAILED DESCRIPTION

Figure 1:
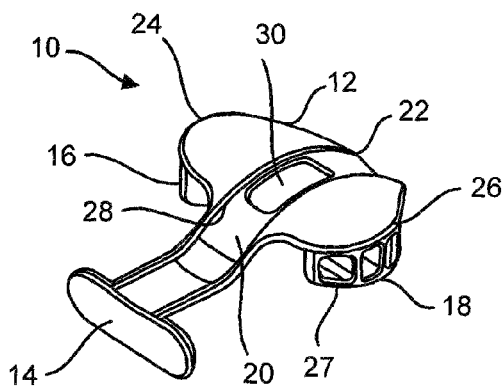
FIG. 1 is a top perspective view of an embodiment of a bilateral bite block according to the invention.
Figure 2:
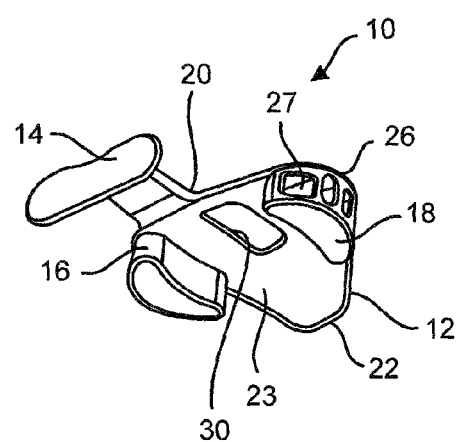
FIG. 2 is a bottom perspective view of the bilateral bite block shown in FIG. 1.
Figure 3:
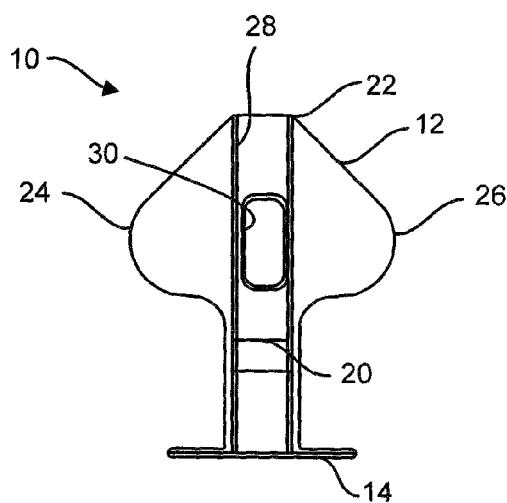
FIG. 3 is a top view of the bilateral bite block shown in FIGS. 1 and 2.
Figure 4:
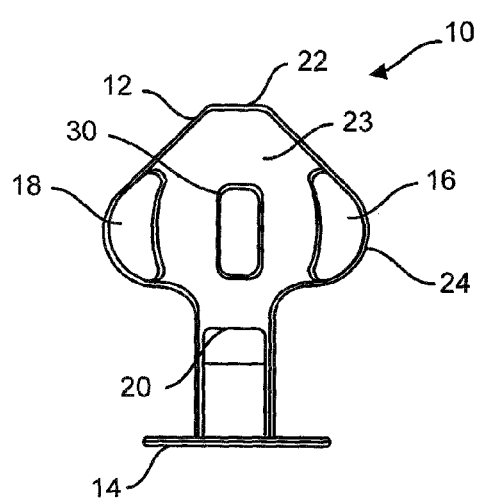
FIG. 4 is a bottom view of the bilateral bite block shown in FIGS. 1 and 2.
Figure 5:
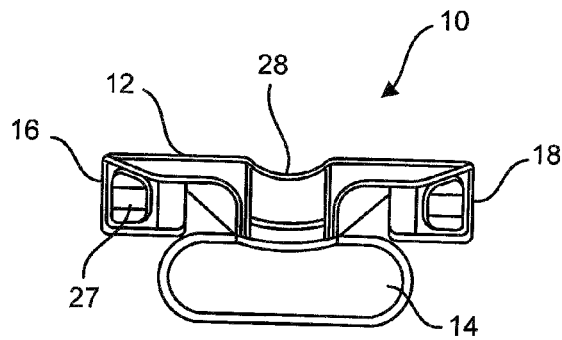
FIG. 5 is a front view of the bilateral bite block shown in FIGS. 1 and 2.
Figure 6:
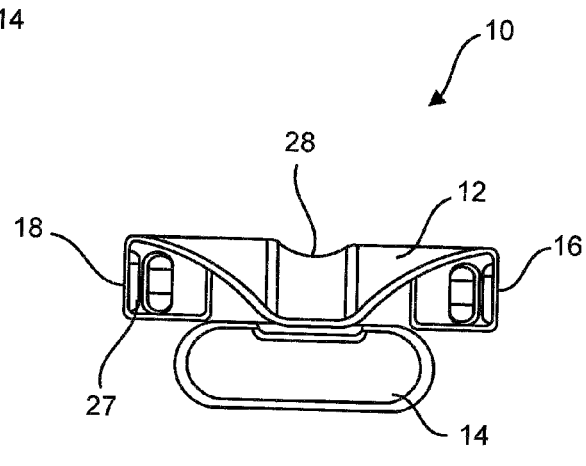
FIG. 6 is a back view of the bilateral bite block shown in FIGS. 1 and 2.
Figure 7:
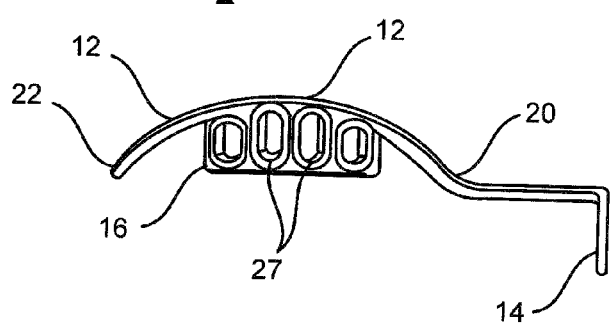
FIG. 7 is a left side view of the bilateral bite block shown in FIGS. 1 and 2.
Figure 8:
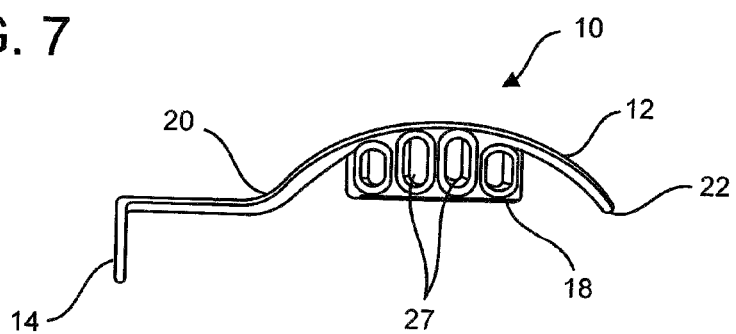
FIG. 8 is a right side view of the bilateral bite block shown in FIGS. 1 and 2.

Referring to the Drawing, an embodiment of a bilateral bite block 10 according to the invention includes a broad upper component 12, a handle 14 and two molar blocks 16, 18.

The broad upper component 12 extends bilaterally between a front end 20 and a back end 22 of the component 12 for overlying a person's tongue and at least some of the person's lower molars and for underlying at least some of the person's upper molars when the bilateral bite block 10 is inserted into the person's mouth. The lower surface 23 of the upper component 12 is smooth so as not to irritate the person's tongue when the upper component 12 is in contact with the tongue.

The molar blocks 16, 18 extend downward from the opposite lateral sides 24, 26 of the broad upper component 12. The molar blocks 16, 18 are disposed for contacting the person's lower molars when the bilateral bite block 10 is inserted into the person's mouth and the person's jaw is closed. When the person's jaw is then closed, the lower molars contact the molar blocks 16, 18 and cause the broad upper component 12 to move into contact with the overlying upper molars and thereby prevent the upper molars from contacting the lower molars.

The molar blocks 16, 18 contain a plurality of voids 27 so that the molar blocks are pliable for cushioning contact with the molars.

The handle 14 extends from the front end 20 of the broad upper component 12 for use in inserting the bilateral bite block 10 into the person's mouth. In the embodiment shown in the drawing, the handle 14 is an integral extension of the broad upper component 12. In other embodiments, the handle 14 is not an integral extension of the broad upper component 12, but instead is attached to the broad upper component 12.

There is a groove 28 extending within the top surfaces of the handle 14 and the upper component 12 for receiving an endotracheal tube in a position that is laterally disposed approximately midway between the person's molars when the bilateral bite block 10 is inserted into the person's mouth and the person's jaw is closed. The groove 28 can be used to guide an endotracheal tube into a person's throat. When an endotracheal tube is received within the groove 28 and into the throat, the combination of the groove 28 and the endotracheal tube inhibits lateral movement of the bilateral bite block 10.

An aperture 30 is disposed within the groove 28 in the upper component 12 for grasping an endotracheal tube that is disposed within the groove 28, to thereby further inhibit lateral movement of the bilateral bite block 10. The upper surface of the upper component 12 next to the aperture 30 is somewhat longitudinally convex to thereby define a deeper aperture 30 for enhancing the grasp of the endotracheal tube by the groove 28.

In the embodiment shown in the drawing, the aperture 30 passes through the upper component 12 so that an endotracheal tube within the groove 28 can contact the person's tongue and thereby enhance the grasp of the endotracheal tube.

In other embodiments (not shown), an aperture is not disposed in the groove 28 and/or does not pass through the upper component 12.

In still other embodiments the various aspects of the different embodiments described herein are combined with one another to the extent that they are not incompatible with each other.

The benefits specifically stated herein do not necessarily apply to every conceivable embodiment of the present invention. Further, such stated benefits of the present invention are only examples and should not be construed as the only benefits of the present invention.

While the above description contains many specificities, these should not be construed as limitations on the scope of the present invention, but rather as examples of the preferred embodiments described herein. Other variations are possible and the scope of the present invention should be determined not by the embodiments described herein but rather by the claims and their legal equivalents.

The invention claimed is:

1. A bilateral bite block, comprising:
a broad upper component extending bilaterally between a front end and a back end of the broad upper component for overlying a person's tongue and at least some of the person's lower molars and for underlying at least some of the person's upper molars when the bilateral bite block is inserted into the person's mouth;
molar blocks extending downward from both sides of the broad upper component and disposed for contacting the person's lower molars when the bilateral bite block is inserted into the person's mouth and the person's jaw is closed; and
a handle extending from the front end of the broad upper component for use in inserting the bilateral bite block into the person's mouth;
wherein there is a groove extending within a top surface of the broad upper component for receiving an endotracheal tube in a position that is laterally disposed approximately midway between the person's molars when the bilateral bite block is inserted into the person's mouth and the person's jaw is closed;
wherein an aperture is disposed within the groove in the broad upper component for grasping a received endotracheal tube that has been received within the groove, to thereby inhibit lateral movement of the bilateral bite block;
wherein the top surface of the broad upper component next to the aperture is longitudinally convex to thereby define the aperture for enhancing said grasp of said received endotracheal tube; and
wherein the aperture passes through the broad upper component so that said received endotracheal tube that extends within the groove can contact the person's tongue and thereby enhance said grasp of said received endotracheal tube.

2. A bilateral bite block, comprising:
a broad upper component extending bilaterally between a front end and a back end of the broad upper component for overlying a person's tongue and at least some of the person's lower molars and for underlying at least some of the person's upper molars when the bilateral bite block is inserted into the person's mouth;
molar blocks extending downward from both sides of the broad upper component and disposed for contacting the person's lower molars when the bilateral bite block is inserted into the person's mouth and the person's jaw is closed; and
a handle extending from the front end of the broad upper component for use in inserting the bilateral bite block into the person's mouth;
wherein there is a groove extending within a top surface of the broad upper component for receiving an endotracheal tube in a position that is laterally disposed approximately midway between the person's molars when the bilateral bite block is inserted into the person's mouth and the person's jaw is closed;
wherein an aperture is disposed within the groove in the broad upper component for grasping a received endotracheal tube that has been received within the groove, to thereby inhibit lateral movement of the bilateral bite block; and
wherein the aperture passes through the broad upper component so that said received endotracheal tube that extends within the groove can contact the person's tongue and thereby enhance said grasp of said received endotracheal tube.

* * * * *